US008501477B2

(12) United States Patent
Short et al.

(10) Patent No.: US 8,501,477 B2
(45) Date of Patent: Aug. 6, 2013

(54) KIT INCLUDING SUBSTRATES WITH VARIOUS SURFACE CHEMISTRIES

(71) Applicant: Corning Incorporated, Corning, NY (US)

(72) Inventors: Robert Short, West Lakes Shore (AU); Patricia Murray, Liverpool (GB); Kristina Parry, Rotherham (GB)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/629,893

(22) Filed: Sep. 28, 2012

(65) Prior Publication Data

US 2013/0023003 A1 Jan. 24, 2013

Related U.S. Application Data

(62) Division of application No. 12/233,127, filed on Sep. 18, 2008, now Pat. No. 8,288,118.

(60) Provisional application No. 60/973,638, filed on Sep. 19, 2007.

(51) Int. Cl.
*C12N 5/00* (2006.01)

(52) U.S. Cl.
USPC .......................... 435/402; 435/377; 435/299.1

(58) Field of Classification Search
None
See application file for complete search history.

(56) References Cited

U.S. PATENT DOCUMENTS

| 4,919,659 | A | 4/1990 | Horbett et al. |
| 5,455,040 | A | 10/1995 | Marchant |
| 5,545,531 | A | 8/1996 | Rava et al. |
| 5,720,341 | A | 2/1998 | Watanabe et al. |
| 5,964,282 | A | 10/1999 | Seiler et al. |
| 5,976,466 | A | 11/1999 | Ratner et al. |
| 6,042,875 | A | 3/2000 | Ding et al. |
| 6,306,506 | B1 | 10/2001 | Timmons et al. |
| 2003/0113478 | A1 | 6/2003 | Dang et al. |
| 2005/0164377 | A1 | 7/2005 | Miyabayashi et al. |
| 2008/0003659 | A1 | 1/2008 | Short et al. |

FOREIGN PATENT DOCUMENTS

| EP | 0124200 A2 | 11/1984 |
| EP | 0249513 A2 | 12/1987 |
| JP | 08159686 | 6/1996 |
| WO | 9000343 | 1/1990 |
| WO | 9410938 | 5/1994 |
| WO | 9636877 | 11/1996 |
| WO | 0078928 A2 | 12/2000 |
| WO | 0131339 A1 | 5/2001 |
| WO | 0145862 A1 | 6/2001 |
| WO | 0232591 A2 | 4/2002 |
| WO | 02053299 A1 | 7/2002 |
| WO | 03030958 A1 | 4/2003 |
| WO | 03035850 A2 | 5/2003 |
| WO | 03053489 A2 | 7/2003 |
| WO | 03082483 A1 | 10/2003 |
| WO | 2004018654 A2 | 3/2004 |
| WO | 2004040308 A1 | 5/2004 |
| WO | 2004111648 A2 | 12/2004 |
| WO | 2005099894 A1 | 10/2005 |
| WO | 2007113587 A2 | 10/2007 |

OTHER PUBLICATIONS

Chu et al., "Plasma-surface modification of biomaterials", Materials Science and Engineering R 36 (2002), pp. 143-206.
Fraser et al., "A Multi-Technique Investigation of the Pulsed Plasma and Plasma Polymers of Acrylic Acid: Millisecond Pulse Regime", J. Phys. Chem. B, 2002, vol. 106, pp. 5596-5603.
Goessl et al., "Plasma lithography-thin-film patterning of polymers by RF plasma polymerication II: Study of differential binding using adsorption probes", J. Biomater. Sci. Polymer Edn, vol. 12, No. 7, pp. 739-753 (2001).
Horak, D. et al., "Poly(2-hydroxyethyl methacrylate)-Based Slabs as a Mouse Embryonic Stem Cell Support", Biomaterials, Elsevier Science Publishers BV, Barking, GB, vol. 25, No. 22, Oct. 1, 2004, pp. 5249-5260.
Konno, T. et al., "Culture of Mouse Embryonic Stem Cells on Photoimmobilized Polymers", Journal of Bioscience and Bioengineering, Elsevier, Amsterdam, NL, vol. 102, No. 4, Oct. 1, 2006, pp. 304-310.
Ogumi et al., "Functionally gradient polymer electrolyte prepared by plasma polymerization", Solid State Ionics, vol. 121, 1999, pp. 289-293.
O'Toole et al., "Characterization of Plasma Polymers of Acrylic Acid and Propanoic Acid", Macromolecules, 1996, vol. 29, pp. 5172-5177.
Whittle et al., "A method for the deposition of controllable chemical gradients", Chemical Comms, Jul. 21, 2003, vol. 9, No. 14; pp. 1766-1767.

*Primary Examiner* — Jim Ketter
(74) *Attorney, Agent, or Firm* — Hoffmann & Baron, LLP

(57) ABSTRACT

In one embodiment of the invention, there is provided a kit including: (i) a plasma polymerized surface having first and second regions, said first region including a first concentration of carboxylic acid groups on said plasma polymerized surface and said second region including a second concentration of carboxylic acid groups on said plasma polymerized surface, wherein said first concentration and said second concentration are different; (ii) a first plasma polymerized secondary substrate having carboxylic acid groups disposed consistently thereacross at a concentration equal to said first concentration; and, (iii) a second plasma polymerized secondary substrate having carboxylic acid groups disposed consistently thereacross at a concentration equal to said second concentration.

7 Claims, 5 Drawing Sheets

(a)

(b)

(a) (b)

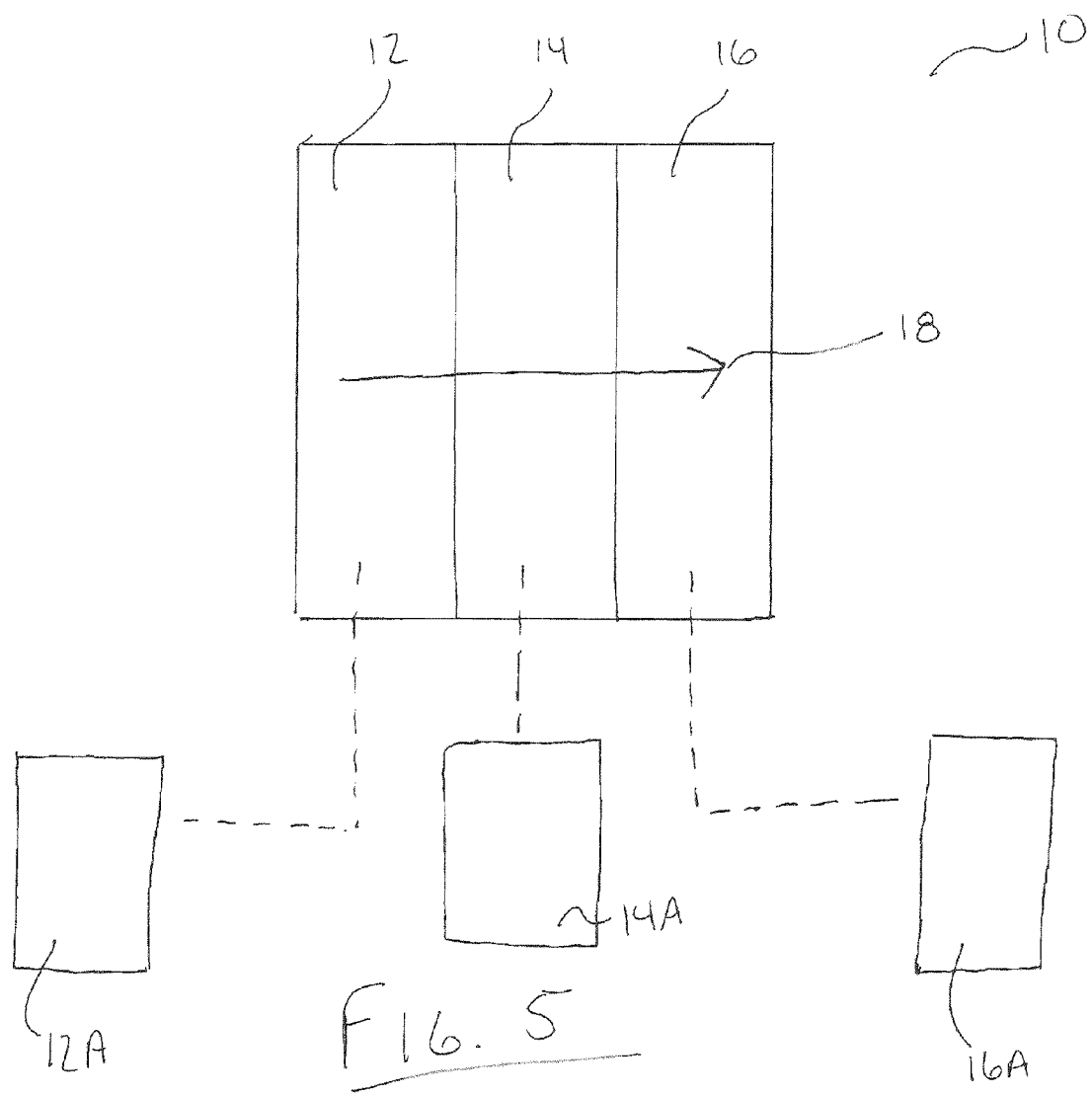

KIT INCLUDING SUBSTRATES WITH VARIOUS SURFACE CHEMISTRIES

CROSS-REFERENCE TO RELATED APPLICATIONS

This application is a divisional application of U.S. application Ser. No. 12/233,127, filed Sep. 18, 2008, now allowed, which claims priority to U.S. Provisional Patent Application No. 60/973,638, filed Sep. 19, 2007, the entire contents of which are hereby incorporated by reference.

FIELD OF THE INVENTION

The invention relates to a substrate for culturing mammalian stem cells, in particular embryonic stem cells.

The process by which a whole organism made up of large numbers of different cell types is produced from a single fertilised egg is complex, involving structural and environmental differences between cells as they grow and divide. The resulting differentiated cell types maintain their phenotype as a result of the interplay between cell-cell interactions, the circulating environmental signals (pH, small molecules, dissolved gases, proteins etc) and the programmed expression of the cellular genome, itself influenced by epigenetic changes brought about by the process of differentiation.

The ex vivo growth of eukaryotic cells derived from multicellular organisms inevitably represents an approximation to the naturally occurring in vivo conditions and unsurprisingly there are many areas where the current techniques are found wanting. Although mammalian cell culture is a multibillion dollar business, as measured both by the value of its products such as therapeutic proteins (e.g. interferons, humanised monoclonal antibodies, protein hormones) as well as the equipment and consumables required to carry out the process, the successes represent only a small and distinct sub-set of all cell types. Typically, large-scale mammalian culture uses cells that have been selected to grow well in the conditions used and the end use (e.g. high-level production of a valuable protein) does not require a highly differentiated cell line. Many widely used cell culture lines are derived from neoplastic tissues and are said to be transformed, that is their genetic material has been mutated (by insertion, deletion or rearrangement) to remove normal controls on cell growth and as such they are atypical of normal differentiated cells.

For a wide range of applications in fundamental biological research as well as the development of novel therapies such as tissue engineering and organ replacement it would be advantageous to be able to better emulate the natural in vivo cellular environment.

Recently there has been a tremendous interest in undifferentiated cells known as stem cells because these are potentially able to differentiate into either all other cell types (totipotent cells) or certain cell lineages (pluripotent cells). For these cells the challenge is to provide culture conditions that allow the propagation of the undifferentiated cells whilst retaining their ability to differentiate.

Typically in vitro cell culture uses plastic vessels to support the growth of the cells and provide a receptacle within which the cells can be exposed to a controlled environment (temperature, pH, dissolved gases etc) and surrounded by a defined culture medium, typically an aqueous solution of salts, buffers and proteins but supplemented with biologically-derived materials (e.g. foetal calf serum, serum albumin, "growth factors"). In this situation the plastic inner surface of the vessel is not a passive component of the system but rather is a key factor influencing the behaviour of the cells as they contact it. In vivo, cells are in contact with either multiple other cells (of either the same or different phenotype) or with biological support materials (bone, cartilage) or with biological fluids (blood, cerebrospinal fluid). Whilst many of the contacts involve specific signalling through the medium of cell surface receptors and the receptor agonists/antagonists, there is also a more general requirement for a particular surface chemistry that enables the cell to first attach, then form focal contacts and finally adopt a phenotypic morphology. In culture, it is ideal if cells proliferate, without differentitation, possibly over many passages. An important requirement of tissue culture plasticware would be to provide the most appropriate surface chemistry for a given cell type.

Polystyrene is the most commonly used material for the fabrication of tissue culture plasticware because of its physical properties (moldability, rigidity, transparency for microscopic examination of the culture) and affordability. However, the natural surface of polystyrene is not biocompatible because it is too hydrophobic for good cell attachment and growth. All tissue culture plasticware is therefore treated before use and there are many approaches to making improved polystyrene surfaces.

The most commonly used approach is to reduce the hydrophobicity of the surface by exposing it to processes such as corona discharge and gas plasmas (oxygen or argon). Whilst these approaches have been commercially successful and have improved the biocompatibility of the polystyrene surface, they simply modify the existing surface and do not provide a range of different surface chemistries. In particular, they do not in themselves address the need for surfaces suitable for the highly differentiated cell types discussed above nor for stem cells.

Further modification of the surface can be carried out by the adsorption of materials to provide a coating that separates the surface from direct contact with the cells. Examples of this are treatment with poly-lysine, which produces a positively-charged surface, or with collagen, fibrinogen or extracellular matrix (a preparation of a complex of proteins and carbohydrates found on the surface of cultured cells) that mimic naturally occurring interfaces. For stem cells it is common to use a pre-attached layer of feeder cells (fibroblasts) to provide a more suitable surface for attachment and growth.

It has proved difficult to control stem cell differentiation; cells will spontaneously differentiate in culture. It is equally difficult to promote specific differentiation: efficiency is low and many cells are lost, and some cells fail to differentiate. Uncontrolled differentiation presents a very specific problem with the use of stem cells in cell therapy, as there may be the potential for cells to form tumours. Feeder layer cells have been used to support the culture of stem cells, and to control cell differentiation. WO2004/018654 discloses a method for the culture of human adult stem cells (keratinocytes) which uses a feeder layer of mouse fibroblasts to support the culture of the cells. In accordance with the Guidelines for GMP for investigational medicinal products for human use (EU directive 2003/94EC), it is desirable to remove all animal derived material.

There is a need for improved cell culture surfaces to facilitate the culture of certain cell types.

SUMMARY OF THE INVENTION

In one embodiment of the invention, there is provided a method of analyzing various surface chemistries for culturing a particular cell line, which includes the steps of: (1) providing a plasma polymerized surface having first and second regions, the first region including a first concentration of carboxylic acid groups in the plasma polymerized surface and the second region including a second concentration of carboxylic acid groups in the plasma polymerized surface, wherein the first and second concentrations are different; (2) culturing cells from the cell line on the plasma polymerized surface in each the region; (3) observing activity of the cultured cells in each the region; and (4) analyzing the activity of the cultured cells in each region.

BRIEF DESCRIPTION OF THE FIGURES

The invention will now be described with reference to the following non-limiting example in which:

FIG. 5 is a representation of one embodiment of a cell culture surface having a plurality of regions of carboxylic acid levels.

DETAILED DESCRIPTION OF THE INVENTION

Figure 1:
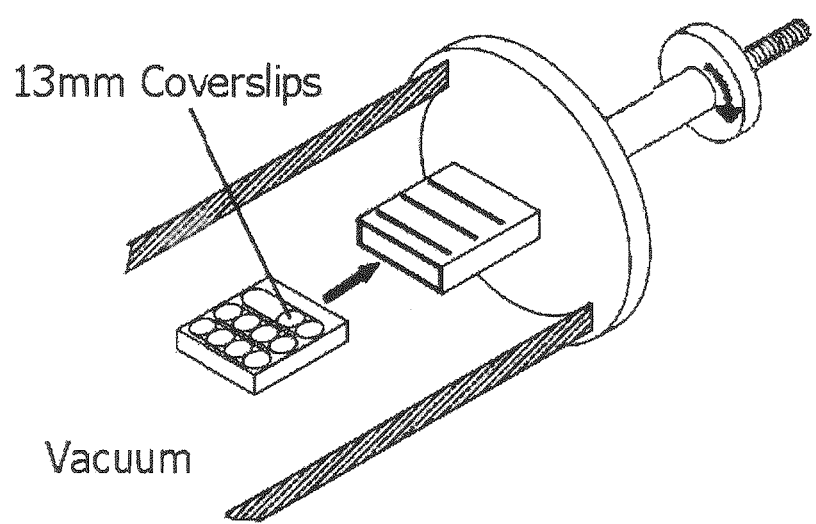
FIG. 1 is a representation of one embodiment of a drawer mechanism for depositing plasma polymer onto a substrate.

According to a first aspect of the invention there is provided a cell culture surface comprising a substrate and a polymer of a carboxylic acid wherein the carboxylic acid concentration of the polymer is between 3% and 33%. The percentages refer to the percent of carbon atoms that are carboxylic acid groups. For example, 3-33% means that 3-33 carbon atoms per one hundred carbon atoms are carboxylic acid groups. The carboxylic acid content of a cell culture product is determined by methods described herein and methods known in the art. For example, percent carboxylic acid content may be measured by X-ray photoelectron spectroscopy.

The polymer provides a cell culture surface on at least part of the surface of the substrate and it has, surprisingly, been found that such a cell culture surface provides for mammalian cell attachment, but restricts the degree of cell spreading, and hence maintains stem cells such as embryonic stem cells in a proliferative but undifferentiated state.

A carboxylic acid concentration of between 3% and 33% equates to a carboxylic acid group density of approximately $5.1 \times 10^{13}$-$5.7 \times 10^{14}$ per $cm^2$.

In a preferred aspect of the invention, the polymer comprises a carboxylic acid concentration of between 5% and 20%, for example 7-20%. The polymer may comprise a carboxylic acid concentration of 7-13% or 14-16%.

In a preferred embodiment of the invention the polymer comprises a carboxylic acid concentration of from 8-15%.

In a preferred aspect of the invention, the polymer comprises a carboxylic acid concentration of between 5% and 10%, for example 8-10%.

In a preferred aspect of the invention, the polymer comprises a carboxylic acid concentration of between 10% and 20%, for example 10-15%. The polymer may comprise a carboxylic acid concentration of 10%-12% or 12-14%.

In a preferred aspect of the invention, the polymer comprises a carboxylic acid concentration of between 15 and 20%. The polymer may comprise a carboxylic acid concentration of 16-18% or 18-20%.

In a preferred aspect of the invention the polymer is obtained from the group of carboxylic acid containing monomers consisting of acrylic acid, methacrylic acid, acetic acid and vinylacetic acid including any vinylic monomer containing a carboxylic acid that is polymerisable. Preferably the carboxylic acid-containing monomer is acrylic acid monomer. The polymer may consist of a single carboxylic acid-containing monomer. Preferably the polymer is a co-polymer of a carboxylic acid containing monomer and one or more monomers. The co-polymer may comprise at least one carboxylic acid-containing monomer with at least one monomer selected from a hydrocarbon, acid, alcohol or amine. Preferably the polymer is a co-polymer of a carboxylic acid and a hydrocarbon, the hydrocarbon being used to control the carboxylic acid density of the resultant polymer.

Preferably the co-polymer is a co-polymer of a carboxylic acid monomer and an alcohol monomer. More preferably, the alcohol is an allyl alcohol.

Polymerizable monomers that may be used in the copolymer of the invention preferably comprise unsaturated organic compounds such as olefinic amines, halogenated olefins, olefinic carboxylic acids and carboxylates, olefinic nitrile compounds, oxygenated olefins and olefinic hydrocarbons. Such olefins include vinylic and allylic forms. The monomer need not be olefinic, however, to be polymerizable. Cyclic compounds such as cyclohexane, cyclopentane and cyclopropane are commonly polymerizable in gas plasmas by glow discharge methods. Derivatives of these cyclic compounds, such as 1, 2-diaminocyclohexane for instance, are also commonly polymerizable in gas plasmas.

Particularly preferred monomers for use in the copolymer of the invention are polymerizable monomers of allylamine. Mixtures of polymerisable monomers may be used. Additionally, polymerisable monomers may be blended with other gases not generally considered as polymerisable in themselves, examples being argon, nitrogen and hydrogen.

Alternative examples of monomers for use in co-polymers of the invention include fully saturated and unsaturated amine compounds up to 20 carbon atoms, more typically 2-8 carbons. Ethylenically unsaturated compounds (especially primary, secondary or tertiary amines) include allylamine. Saturated monomers include methylamine, propylamine, heptylamine and diaminopropane.

The cell culture surface may comprise a polymer that is a co-polymer of acrylic acid and one or more acrylic acid ester including but not limited to acrylic acid amides, methacrylates, acrylonitrile, vinyl, styrene and butadiene. An example of a copolymer of acrylic acid is ethylene-acrylic acid copolymer.

The polymer may comprise an amine co-polymer. The co-polymer may be prepared by the plasma polymerisation of an organic amine with a saturated (alkane) or unsaturated (alkene, diene or alkyne) hydrocarbon.

In a preferred embodiment the polymer is a co-polymer of a carboxylic acid monomer and a hydrocarbon monomer, preferably 1,7-octadiene. Alternative examples of hydrocarbons may be of up to 20 carbons (but more usually of 4-8). Examples of alkanes are butane, pentane and hexane. Examples of alkenes are butene and pentene. An example of a diene is 1-7 octadiene. The co-polymer may also be aromatic-containing e.g. styrene.

Co-polymerisation may be carried out using any ratio of amine:hydrocarbon, but will be typically using an amine:

hydrocarbon ratio between the limits of 100 (amine):0(hydrocarbon) to 20 (amine):80 (hydrocarbon) and any ratio between these limits.

The density of carboxylic acid groups in the polymer of the cell culture surface may be calculated from the density of the polymer. For example, where the polymer is plasma polymerised acrylic acid, the density of plasma polymerised acrylic acid may be in the range of 1.5-1.7 g/cm$^3$ (more specifically 1.6 g/cm$^3$).

In a preferred embodiment the polymer is deposited on the surface.

According to a further aspect of the invention there is provided a cell culture surface comprising a substrate and a polymer coating on at least part of the surface of the substrate, said coating representing a polymer gradient wherein the carboxylic acid content of the polymer varies from 0% to 33%. The polymer gradient is preferably characterized by a chemical gradient or a polymer composition gradient, most preferably a carboxylic acid gradient. The gradient may be a two dimensional gradient or preferably extends into three dimensions, wherein the X-Y plane is defined by the surface, and the Z-direction is substantially perpendicular thereto. Note that 0% carboxylic acid content means that no carbon atoms per 100 carbon atoms have carboxylic acid functionality. The polymer coating may comprise a polymer gradient in which the carboxylic acid content of the polymer varies from 2% to 33%. Preferably the surface of the substrate is a substantially plane surface area and the polymer gradient is essentially parallel to the plane of the surface of the substrate.

A cell culture product of the present invention comprises a cell culture surface of the invention. In addition, a cell culture product according to the invention may comprise a cell culture medium which does not contain serum. The cell culture medium may be supplemented with an agent that promotes cell proliferation without differentiation such as a mitogen, for example human leukaemia inhibitory factor (LIF), or a growth factor such as a human growth factor, for example, human epidermal growth factor or human basic fibroblast growth factor. Preferably the cell culture medium does not contain a mitogen. Preferably still the culture medium does not contain a growth factor.

The requirement in cell culture for a complex culture medium which typically contains either biological fluids (e.g. foetal calf serum) or specific biomolecules (growth factors) intended as serum replacements is both expensive and requires extensive and expensive quality control testing before it can be used. Moreover, the use of such biological supplements introduces the possibility of contamination with infectious agents (viruses, prions), raising significant safety issues for any resultant therapy. Thus the absence of serum in the cell culture medium is desirable. For stem cells, the presence of feeder cells in the cultures raises similar issues about the purity, homogeneity and safety of derived cells. Thus, in a preferred aspect of the invention the cell culture receptacle does not contain feeder cells.

In a preferred embodiment of the invention the cell culture product comprises a cell culture medium that is sufficient to support the growth of mammalian cells but which does not include either serum or feeder cells. In a further preferred embodiment of the invention the cell culture product comprises a serum free cell culture medium that does not include feeder cells and does not include a mitogen such as LIF.

The cell culture substrate may comprise a non-porous polymer; for example the substrate may be a solid phase substrate such as a plastics or a glass substrate. The substrate may be a porous or fibrous material such as a woven or non-woven material. Examples of substrate include, but are not limited to, particles such as nano-particles, beads (e.g polymeric, glass), tapes, ribbons, fibres, polymer films, gels and textiles. The substrate may consist of the carboxylic acid containing polymer, for example the substrate may be a scaffold (for example for tissue engineering) formulated from the carboxylic acid containing polymer. For example, the substrate may be a non-woven mesh of the carboxylic acid containing polymer.

As used herein the term "cell culture product" refers to any means suitable for carrying out mammalian cell culture. The cell culture product may be a cell culture receptacle including but not limited to a Petri dish, cell culture flask, multiwell plate or microwell plate.

The term "receptacle" is intended to include any means suitable for containing mammalian cell culture. Alternatively the cell culture product may be a cell culture substrate as defined herein. Thus a further aspect of the invention provides a cell culture substrate comprising a cell culture surface wherein said surface comprises a polymer of a carboxylic acid in which the carboxylic acid content of the polymer is between 3% and 33%.

In a further aspect, the invention provides a process of preparing a cell culture surface, comprising applying a polymer of a carboxylic acid containing monomer source to a cell culture substrate, wherein the carboxylic acid concentration of the polymer is from 3% to 33%.

A further aspect of the invention provides a process to treat a cell culture substrate comprising the steps of
  i) providing a cell culture substrate;
  ii) providing at least one carboxylic acid containing monomer source;
  iii) applying the monomers onto the surface of the substrate; and
  iv) polymerising the monomer to provide a cell culture substrate comprising a polymer of a carboxylic acid wherein the carboxylic acid concentration of the polymer is between 3% and 33%.

In a preferred embodiment the process comprises the steps of:
  i) contacting the cell culture substrate with a carboxylic acid containing monomer source; and
  ii) polymerizing the monomer source to provide a polymer, wherein the carboxylic acid concentration of the polymer is from 3% to 33%.

The carboxylic acid containing monomer sources may comprise a 30-99% acid monomer, for example acrylic acid monomer. The acid monomer source may consist of a 100% acid monomer source, for example 100% acrylic acid source.

According to a further aspect of the invention there is provided a method to treat a cell culture substrate comprising the steps of
  i) providing a cell culture substrate;
  ii) providing at least one monomer source containing a carboxylic acid and a hydrocarbon wherein the carboxylic acid and hydrocarbon are provided as a mixture or separate monomer sources;
  iii) applying the monomers onto the surface of the substrate; and
  iv) polymerising the monomer to provide a cell culture substrate comprising a carboxylic acid co-polymer wherein the carboxylic acid concentration of the co-polymer is between 3% and 33%.

In a preferred embodiment said polymer application comprises the steps of:
  i) creating a plasma of the carboxylic acid containing monomer source;
  ii) contacting the cell culture substrate with said plasma.

Thus a further aspect of the invention provides a process of preparing a cell culture surface according to the first aspect of the invention, the process comprising the steps of:
 i) providing at least one carboxylic acid containing monomer source in a gas feed;
 ii) creating a plasma of said monomer; and
 iii) bringing into contact a cell culture substrate with the plasma of (ii) to provide a cell culture product comprising a carboxylic acid polymer wherein the carboxylic acid concentration of the co-polymer is between 3% and 33%.

Preferably the method further comprises providing a cell culture product comprising the treated cell culture substrate.

The polymerisation of the monomer may include methods known in the art including, but not limited to, radical, anionic or cationic polymerisation; group transfer (GT) polymerisation; surface graft polymerisation including atom transfer (surface initiated) radical polymerisation; UV (photon) graft polymerisation, plasma-initiated graft polymerisation or plasma polymerisation. The polymer may be applied to surface of the substrate post-polymerisation (for example from a solvent) or more likely during polymerisation, as with UV graft, plasma-initiated graft or plasma polymerisation. Suitable plasma polymerization methods include those described in PCT Publication Nos. WO 2004/111648 and WO 2003/082483, the contents of both of which are incorporated herein by reference.

Preferably the polymerisation of the monomer is carried out using plasma polymerisation. Thus, in the methods of the invention the monomers are provided in a gas feed and a plasma is created of said monomer or monomer mixture.

The carboxylic acid containing monomer sources may comprise a 30-99% acid monomer, for example acrylic acid monomer. The acid monomer source may consist of a 100% acid monomer source, for example 100% acrylic acid source.

Plasma polymerisation is a technique which allows an ultra-thin (e.g. ca. 200 nm) cross linked polymeric film to be deposited on substrates of complex geometry and with controllable chemical functionality. As a consequence, the surface chemistry of materials can be modified, without affecting the bulk properties of the substrate so treated. Plasmas or ionised gases are commonly excited by means of an electric field. They are highly reactive chemical environments comprising ions, electrons, neutrals (radicals, metastables, ground and excited state species) and electromagnetic radiation. At reduced pressure, a regime may be achieved where the temperature of the electrons differs substantially from that of the ions and neutrals. Such plasmas are referred to as "cold" or "non-equilibrium" plasmas. In such an environment many volatile organic compounds (e.g. volatile alcohol containing compounds, volatile acid containing compounds, volatile amine containing compounds, or volatile hydrocarbons, neat or with other gases, e.g. Ar, have been shown to polymerise (H. K. Yasuda, Plasma Polymerisation, Academic Press, London 1985) coating both surfaces in contact with the plasma and those downstream of the discharge. The organic compound is often referred to as the "monomer". The deposit is often referred to as "plasma polymer". The advantages of such a mode of polymerisation potentially include: ultra-thin pin-hole free film deposition; plasma polymers can be deposited onto a wide range of substrates; the process is solvent free and the plasma polymer is free of contamination.

Thin polymeric films can be obtained from the plasmas of volatile organic compounds (at reduced pressure of $1-1\times10^{-3}$ mbar and ideally less than 100° C.). Preferably the monomer is a polymerisable monomer having a vapour pressure of at least $6.6\times10^{-2}$ mbar. Monomers with a vapour pressure of less than $1.3\times10^{-2}$ mbar are generally not suitable unless their vapour pressure can be raised sufficiently by heating.

In plasma polymer deposition, there is generally extensive fragmentation of the starting compound or ionised gas and a wide range of the resultant fragments or functional groups are undesirably incorporated into the deposit. By employing a low plasma input power (low plasma power/monomer flow rate ratio) it is possible to fabricate films with a high degree of functional group retention. Typically, using the composite ratio of W/FM, as described by Yasuda (Plasma Polymerisation, Academic Press, 1985) the power loading should be $<10^9$ J/kg, or more ideally, $<10^8$ J/kg to achieve functional group retention in plasma polymers. (W=Power (J/min), F=Flow rate (mol/min), M=average molecular mass (kg/mol). However, other relatively low ratios may be used and are known to those skilled in the art. Alternatively, plasma polymer deposits may be formed by pulsing the plasmas or ionised gases. Plasmas are formed either from single monomer species or in combination with other organic molecules.

Under conditions of low power ($<10^{-3}$ W/1, ideally $<<10^{-3}$ WA), plasma polymer films can be prepared which retain a substantial degree of the chemistry of the original monomer. For example, plasma polymerised films of acrylic acid contain the carboxyl group (Haddow et al., Langmuir, Vol 16: 5654-60, 2000). The low power regime may be achieved either by lowering the continuous wave power, changing the monomer flow rate, or by pulsing the power on and off. Such low power plasmas typically have a density of less than $10^{17}/m^3$, a criteria which is met during the "on" phase of a pulsed plasma as well as during continuous wave plasma.

Where the cell culture substrate is a glass substrate, the use of a primer layer (for example hexamethyldisiloxane) deposited by plasma may be required.

Co-polymerisation of one or more compounds having functional groups with a hydrocarbon allows a degree of control over surface functional group concentrations in the resultant plasma copolymer (PCP) (Beck et al., Polymer 37: 5537-5539, 1996). Suitably, the monomers are ethylenically unsaturated. Thus the functional group compound is typically carboxylic acid whilst the hydrocarbon is suitably an alkene. By plasma polymerisation, it is also possible to deposit ethylene oxide-type molecules (eg. tetraethyleneglycol monoallyl ether) to form 'non-fouling' surfaces (Beyer et al., Journal of Biomedical Materials Research 36: 181-9, 1997). It is also possible to deposit perfluoro-compounds (i.e. perfluorohexane, hexafluoropropylene oxide) to form hydrophobic/superhydrophobic surfaces (Coulson et al., Chemistry of Materials 12: 2031-2038, 2000).

According to a further aspect of the invention there is provided a method for the culture of mammalian cells comprising the steps of:
 i) providing a cell culture surface according to the invention;
 ii) bringing said cell culture surface into contact with mammalian cells; and
 iii) providing conditions which promote the proliferation of the mammalian cells.

According to a further aspect of the invention there is provided a method for the culture of stem cells comprising the steps of:
 i) contacting stem cells with a cell culture surface according to the invention as described previously; and
 ii) providing conditions which promote the proliferation of the stem cells.

Preferably, the cell surface comprises a cell culture substrate and a polymer comprising a carboxylic acid monomer, wherein the carboxylic acid concentration of the polymer is from 3% to 33%.

In a preferred method of the invention the surface forms part of a cell culture product. More preferably, the cell culture product comprises a cell culture medium which does not contain serum. Preferably the serum free cell culture medium does not contain a mitogen such as LIF. Preferably still the cell culture receptacle does not contain feeder cells.

In a preferred method of the invention the mammalian cells are stem cells, for example, embryonic stem cells. Preferably said cells are human.

In a preferred method of the invention the mammalian cells, for example stem cells, cultured in a product according to the invention are maintained in culture in an un-differentiated state. Preferably said cells are un-differentiated embryonic stem cells such as human embryonic stem cells.

In a further aspect of the invention there is provided the use of a cell culture surface according to the invention described previously in the culture of mammalian cells. Preferably the mammalian cell is a stem cell, especially a human stem cell. Preferably the stem cell is an embryonic stem cell.

Preferably, the cell surface comprises a cell culture substrate and a polymer comprising a carboxylic acid monomer, wherein the carboxylic acid concentration of the polymer is from 3% to 33%.

In a further aspect of the invention there is provided a cell culture surface according to the invention in the screening of polymeric surfaces useful in the culture of mammalian stem cells such as stem cells. Preferably the polymeric surface represents a polymer gradient wherein the carboxylic acid concentration of the co-polymer is between 3% and 33%. Preferably the surface of the substrate is a substantially plane surface area and the polymer gradient is essentially parallel to the plane of the surface of the substrate.

EXAMPLES

A plasma polymerised gradient from monomers of 100% octadiene (OD) to 100% acrylic acid (AA) was produced on 13 mm glass microscope coverslips as described previously. Both mouse and human ES cells were incubated on these coverslips in Advanced Medium and in Advanced Medium supplemented with LIF. This identified an area to which the ES cells attached and remained undifferentiated.

The next stage was to plasma polymerise a series of homogeneous surfaces from the monomer flow composition identified by the gradient, as well as related control surfaces (plasma polymers of 100% AA, 100% OD and 50%/50% AA/OD [percentage values correspond to ratio of monomers in the gas flow]), onto Petri dishes. Mouse and human ES cells were again incubated with and without LIF on the different surfaces but this time two different culture media were used: Advanced medium as before and Animal Component Free medium, which is the same as the Advanced except that Albumax (a purified form of bovine serum albumin designed to reduce the serum requirement of cultured cells) is replaced by polyvinyl alcohol (PVA).

Fabrication of Gradient Coatings

Using a modified version of the drawer mechanism as first described in Chem Comm, 2003, p1766-68 plasma polymerised gradients of octadiene and acrylic acid were deposited onto glass coverslips of 13 mm diameter. The modification to the drawer mechanism allows the substrates to be moved under a slot as the plasma polymer is deposited (FIG. 1).

The plasma polymerisation reactor was a cylindrical glass vessel (approximately 19 cm in length, 10.5 cm in diameter), evacuated to a base pressure of less than $2\times10^{-3}$ mbar with a vacuum pump and liquid nitrogen trap. Radiofrequency power from a 13.56 MHz signal generator was "inductively coupled" to the chamber by an external copper coil via an automatic matching network (Coaxial Power Systems Ltd). Plasma deposition was at an input power of 10 W (continuous wave) and through a 1 mm wide slot. The substrates were moved under the slot in 250 µm steps at a rate of 750 µm per minute via a stepper motor under computer control.

Acrylic acid and octa-1,7-diene were obtained from Aldrich (UK) and were used as received, save several freeze-thaw cycles to remove dissolved gases prior to use. Monomer flow rates were regulated via two computer controlled needle valves (Meggit Avionics). The valves were calibrated for the flow rate of each monomer and then a simple runfile constructed to automate the change in composition of the monomer mixture in the chamber.

Fabrication of Homogenous Coatings

Plasma polymerised coatings were deposited onto various substrates, including 35 mm diameter culture dishes, using a cylindrical stainless steel chamber (50 cm diameter, 50 cm long) evacuated to a base pressure of less than 2×10-3 mbar with a vacuum pump and liquid nitrogen trap. Radiofrequency power from a 13.56 MHz signal generator was "capacitively coupled" to the chamber by a single internal electrode via an automatic matching network (Coaxial Power Systems Ltd).

Acrylic acid and octa-1,7-diene were obtained from Aldrich (UK) and were used as received, save several freeze-thaw cycles to remove dissolved gases prior to use. Monomer flow rates were regulated via needle valves (Meggit Avionics).

| % Octadiene | % Acrylic Acid | Typical % of carbon atoms in a carboxylic acid group | Approximate density of carboxylic acid groups per cm$^2$ |
|---|---|---|---|
| 0 | 100 | 14-20 | $2.4 \times 10^{14}$-$3.5 \times 10^{14}$ |
| 10 | 90 | 12-16 | $2.1 \times 10^{14}$-$2.8 \times 10^{14}$ |
| 20 | 80 | 10-14 | $1.7 \times 10^{14}$-$2.4 \times 10^{14}$ |
| 30 | 70 | 8-12 | $1.4 \times 10^{14}$-$2.1 \times 10^{14}$ |
| 40 | 60 | 6-10 | $1.0 \times 10^{14}$-$1.7 \times 10^{14}$ |
| 50 | 50 | 4-8 | $7.0 \times 10^{13}$-$1.4 \times 10^{14}$ |
| 60 | 40 | 4-6 | $7.0 \times 10^{13}$-$1.0 \times 10^{14}$ |
| 70 | 30 | 4-6 | $7.0 \times 10^{13}$-$1.0 \times 10^{14}$ |
| 80 | 20 | 2-4 | $3.5 \times 10^{13}$-$7.0 \times 10^{13}$ |
| 90 | 10 | 0-2 | 0-$3.5 \times 10^{13}$ |
| 100 | 0 | 0 | 0 |

In some cases a "primer" layer was deposited onto the substrate before the "functional" layer. In some cases this primer layer was plasma polymerised from the monomer hexamethyldisiloxane. In other cases it was plasma polymerised from the same monomer flow composition as the functional layer, but the input power to the plasma was higher (typically 20W for the primer layer and 7W for the functional layer).

Characterisation by X-ray Photoelectron Spectroscopy

Some gradient coatings were characterized using a Theta Probe XPS instrument from Thermo Electron. This instrument uses a focused, monochromated X-ray beam. Al Kα radiation was used throughout the work (photon energy 1486.6 eV). For this work, an X-ray spot size of 400 µm was used. The Theta Probe is configured with an automated 5 axis sample manipulation; this allows the acquisition of both linescan and mapping data. The linescan contained a total of 25 points covering a distance of 12 mm. Each linescan point represents a set of 16 angle resolved spectra. The gradients were mapped using the snapshot acquisition mode using the angle integrated lens operation. The maps each contain a single angle integrated spectrum at each point. Mapping area 7×12 mm, 500 µm step, 15×25 Pixels.

Some gradient surfaces were analysed using the Axis Ultra XPS instrument from Kratos Analytical (Manchester, UK), using a focused monochromated aluminium X-ray source with photon energy of 1486.6 eV and aperture slot of 300× 700 µm. The linescan consisted of 8 points taken at 1.5 mm intervals across the 13 mm sample. All curve fitting and quantification was performed using the VISION 2 processing software provided with the Instrument.

Some homogeneous surfaces were analysed using a Kratos Analytical AMICUS XPS instrument (Kratos Analytical, Manchester, UK). All XPS analysis was made using a Mg Ka x-ray source operated at 120 W (12 kV, 10 mA), with energy analysis performed using the "Dupont"-type analyzer, featuring a low-pass/high-pass filter design. Survey scans were acquired using a 0.5 eV step size, while narrow scans were acquired using a 0.05 eV step size. All curve fitting and quantification was performed using the VISION 2 processing software provided with the Instrument.

Standard Culture Conditions for E14 and R1 Mouse Embryonic Stem (mES) Cell Lines mES cell lines were maintained on STO feeder cells in DMEM supplemented with 15% (v/v) ES cell-tested FBS (PAA laboratories), 1,000 U/ml LIF (Chemicon), 1 mM L-glutamine, 5 µM 2-mercaptoethanol, 0.1 mM nonessential amino acids and 1 mM sodium pyruvate.

Standard Culture Conditions for HES-3 Human Embryonic Stem (hES) Cell Line

The commercially available hES cell line HES-3 (ESI) was maintained on STO feeder cells in knockout DMEM supplemented with 15% (v/v) serum replacement (Invitrogen), 1 mM L-glutamine, 5 µM 2-mercaptoethanol, 0.1 mM nonessential amino acids, 1 mM sodium pyruvate and 4 ng/ml FGF2 (Reubinoff et al., *Nat Biotechnol* 18, 399-404 (2000)). Under these conditions, the hES cells were passaged by manually cutting the colonies.

Culture on Standard Surfaces in Serum Free Media Supplemented with LIF mES cell lines E14 and R1 and the commercially available hES cell line HES-3 (ESI) were maintained on serum-coated tissue-culture plastic. Coating procedure was as follows:— 3.5 cm Nunc® tissue culture dishes were coated with 10% (v/v) ES cell-tested FBS (foetal bovine serum) diluted in Advanced® DMEM for 15 min. The FBS was then aspirated and dishes washed once with phosphate-buffered saline (PBS). For replating, cells were dissociated using an enzyme free dissociation buffer (Sigma) and cultured in Advanced® DMEM supplemented with 1,000 U/ml LIF (Chemicon), 1 mM L-glutamine and 5 µM 2-mercaptoethanol.

Culture on Plasma Polymerised Surfaces in Serum Free Media Supplemented with LIF For replating onto plasma polymerised surfaces, cells were dissociated using an enzyme free dissociation buffer (Sigma) and cultured in Advanced® DMEM supplemented with 1,000 U/ml LIF (Chemicon), 1 mM L-glutamine and 5 µM 2-mercaptoethanol.

In order to remove the effect of exposure to serum during maintenance, the cells were passaged 3 times on the plasma polymerised surface before staining.

Culture on Standard Surfaces in Serum free media without LIF mES cell lines E14 and R1 and the commercially available hES cell line HES-3 (ESI) were maintained on serum-coated tissue-culture plastic. Coating procedure was as follows: 3.5 cm Nunc® tissue culture dishes were coated with 10% (v/v) ES cell-tested FBS (foetal bovine serum) diluted in Advanced® DMEM for 15 min. The FBS was then aspirated and dishes washed once with phosphate-buffered saline (PBS). For replating, cells were dissociated using an enzyme free dissociation buffer (Sigma) and cultured in Advanced® DMEM supplemented with 1 mM L-glutamine and 5 µM 2-mercaptoethanol.

Culture on Plasma Polymerised Surfaces in Serum Free Media without LIF

For replating onto plasma polymerised surfaces, cells were dissociated using an enzyme free dissociation buffer (Sigma) and cultured in Advanced® DMEM supplemented with 1,000 U/ml LIF (Chemicon), 1 mM L-glutamine and 5 µM 2-mercaptoethanol.

In order to remove the effect of exposure to serum during maintenance, the cells were passaged 3 times on the plasma polymerised surface before staining Culture on Standard Surfaces in Animal Component Free (ACF) Media Supplemented with LIF The E14 mES cell line and the commercially available hES cell line HES-3 (ESI) were maintained on serum-coated tissue-culture plastic. Coating procedure was as follows:—3.5 cm Nunc® tissue culture dishes were coated with 10% (v/v) ES cell-tested FBS (foetal bovine serum) diluted in Advanced® DMEM for 15 min. The FBS was then aspirated and dishes washed once with phosphate-buffered saline (PBS). For replating, cells were dissociated using an enzyme free dissociation buffer (Sigma) and cultured in ACF media, which is based on the recipe of Johansson and Wiles (Johansson and Wiles *Mol. Cell. Biol*, 15, 141-151 (1995)).

Recipe for ACF is as follows: DMEM (Invitrogen) supplemented with 1,000 U/ml LIF (Chemicon), 1 mM L-glutamine, 5 µM 2-mercaptoethanol, 100 mM monothioglycerol, 10% PVA (Polyvinyl alcohol), 0.1 mM nonessential amino acids, essential amino acids at 1:100 (Invitrogen), Insulin/Transferrin/Selenium at 1:100 (Invitrogen), Lipids at 1:100 (Invitrogen), 1 mM sodium pyruvate.

Culture on Plasma Polymerised Surfaces in Animal Component Free (ACF) Media Supplemented with LIF For replating onto plasma polymerised surfaces, cells were dissociated using an enzyme free dissociation buffer (Sigma) and cultured in Advanced® DMEM supplemented with 1,000 U/ml LIF (Chemicon), 1 mM L-glutamine and 5 µM 2-mercaptoethanol.

In order to remove the effect of exposure to serum during maintenance, the cells were passaged 3 times on the plasma polymerised surface before staining Culture on Standard Surfaces in Animal Component Free (ACF) Medium without LIF The E14 mES cell line and the commercially available hES cell line HES-3 (ESI) were maintained on serum-coated tissue-culture plastic. Coating procedure was as follows: 3.5 cm Nunc® tissue culture dishes were coated with 10% (v/v) ES cell-tested FBS (foetal bovine serum) diluted in Advanced® DMEM for 15 min. The FBS was then aspirated and dishes washed once with phosphate-buffered saline (PBS). For replating, cells were dissociated using an enzyme free dissociation buffer (Sigma) and cultured in ACF media, which is based on the recipe of Johansson and Wiles (Johansson and Wiles *Mol. Cell. Biol*, 15, 141-151 (1995)).

Recipe for ACF is as follows: DMEM (Invitrogen) supplemented with 1 mM L-glutamine, 5 µM 2-mercaptoethanol, 100 mM monothioglycerol, 10% PVA (Polyvinyl alcohol), 0.1 mM non-essential amino acids, essential amino acids at 1:100 (Invitrogen), Insulin/Transferrin/Selenium at 1:100 (Invitrogen), Lipids at 1:100 (Invitrogen), 1 mM sodium pyruvate.

Culture on Plasma Polymerised Surfaces in Animal Component Free (ACF) Medium without LIF For replating onto plasma polymerised surfaces, cells were dissociated using an enzyme free dissociation buffer (Sigma) and cultured in Advanced® DMEM supplemented with 1,000 U/ml LIF (Chemicon), 1 mM L-glutamine and 5 µM 2-mercaptoethanol.

In order to remove the effect of exposure to serum during maintenance, the cells were passaged 3 times on the plasma polymerised surface before staining Immuno-Staining for Oct-4

Cells were fixed in 4% (w/v) paraformaldehyde for 10 mins. at room temperature and were then incubated in blocking solution, consisting of 10% (v/v) normal goat serum (NGS), 0.1% (v/v) Triton in PBS, for 1 hour at room temperature. Cells were incubated overnight at 4° C. in primary antibody solution, consisting of 1/500 dilution of anti-mouse Oct-4 (mouse IgG2b) (Santa Cruz), 0.1% (v/v) Triton in PBS. Following 3×10 min. washes in PBS, the cells were incubated in secondary antibody solution, consisting of 1/1000 dilution of anti-mouse IgG2b-Alexa 488 or -594 (Molecular Probes), 0.1% (v/v) Triton in PBS, for 2 hours at room temperature. For visualization of nuclei, cells were co-stained for 5 mins. at room temperature with DAPI solution, consisting of 1/100,000 dilution of DAPI (Molecular Probes) in PBS. Sections were mounted in fluorescent mounting medium and photographed using a Leitz fluorescence microscope. All digital images were prepared with Adobe Photoshop.

Alkaline Phosphatase Activity

Alkaline phosphatase staining was performed on cells fixed as above. Following fixation, cells were equilibrated in 0.1M Tris buffer pH 9.2 and incubated in alkaline phosphatase staining solution (2 mg Naphthol-AS-MX phosphatase (Sigma) and 10 mg Fast Red TR salt (Sigma) dissolved in 10 mls 0.1M Tris pH 9.2) at room temperature for 30 mins. Co-staining with DAPI was performed as above.

RESULTS

Characterisation of Gradients by XPS

Figure 2:
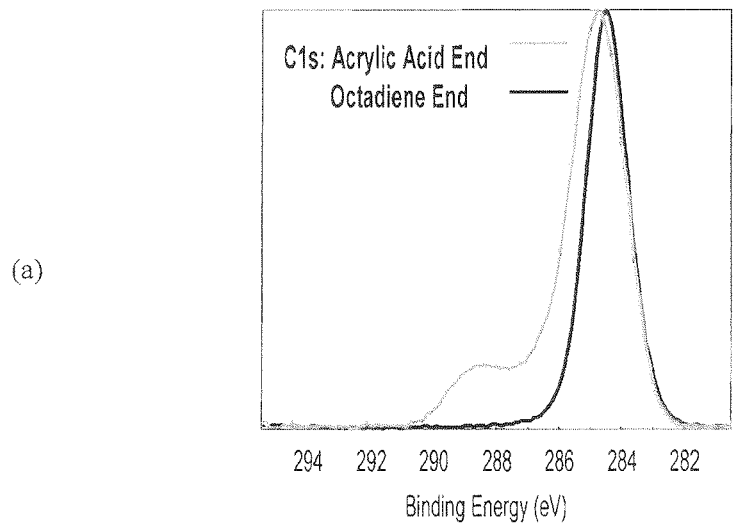
FIG. 2(a)—EPS spectra taken from each end of an octadiene/acrylic acid gradient; (b)—XPS chemical maps taken across a 13 mm octadiene/acrylic acid gradient (X axis)
Figure 2:
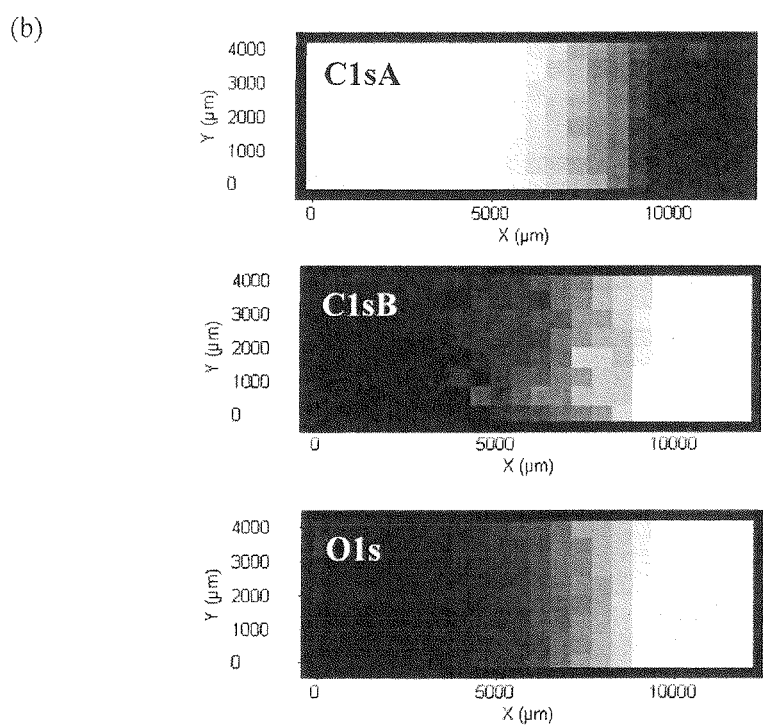

XPS mapping of the gradients demonstrated a smooth transition from hydrocarbon to carboxylic acid surface (FIG. 2). The difference in shape between the two traces indicates the difference in surface chemistry at the two ends of the gradient (FIG. 2(a)). The change in colour scale shows the gradual change from hydrocarbon (C1sA) to oxygen-containing functional groups associated with acrylic acid (C1sB and O1s) (FIG. 2(b)).

Embryonic Stem Cell Culture with LIF

Figure 3:
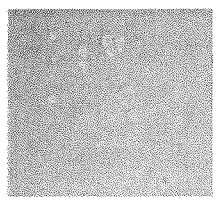
FIG. 3 is a photograph of Human ES cells cultured in serum-free medium (with LIF) on a surface containing carboxylic acid groups where (a) 0% of the carbon atoms are in carboxylic acid groups and (b) 9.8% of the carbon atoms are in carboxylic acid groups.
Figure 3:
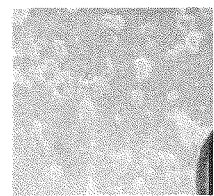

FIG. 3 demonstrates that the amount of carboxylic acid groups in the culture surface affects the number of cells that attach and their morphology. It shows human ES cells cultured in serum-free medium supplemented with LIF on surfaces where a) 0% of the carbon atoms are in carboxylic acid groups and b) 9.8% of the carbon atoms are in carboxylic acid groups.

The cells have a high nuclear to cytoplasmic ratio with prominent nucleoli; they grow in small, tightly clustered colonies with tight phase bright borders. It is difficult to identify individual cells within a colony of undifferentiated ES cells. Differentiated cells, however, have a much lower nuclear to cytoplasmic ratio and the nucleoli are far less prominent.

Alkaline Phosphatase Activity

Figure 4:
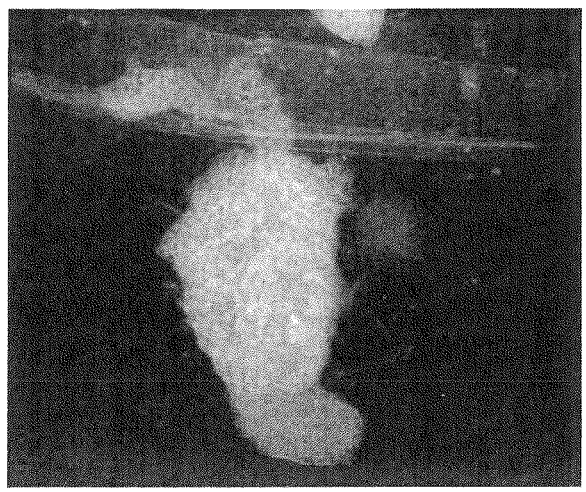
FIG. 4 is a photograph of human ES cells cultured in serum-free media supplemented with LIF on a carboxylic acid containing surface.

Cells that stain positive for alkaline phosphatase are undifferentiated. FIG. 4 shows human ES cells cultured in serum-free media supplemented with LIF on a carboxylic acid containing surface, stained positive for alkaline phosphatase (red). The cells are co-stained with DAPI (blue) for visualisation of nuclei.

Embryonic Stem Cell Culture without LIF

Both human and mouse ES cells cultured on carboxylic acid containing surfaces in the absence of LIF proliferated and remained undifferentiated, as determined by alkaline phosphatase activity and Oct-4 immunostaining (data not shown).

Analyzing Varying Degrees Of Culture Surfaces For Cell Activity

Surface chemical gradients of carboxylic acid functionality may be used to identify an optimal culture surface, on which embryonic stem cells may be cultured, whereby the capacity of these cells for self renewal is maintained by geometric control of cell shape (i.e. cell spreading). Knowing the optimal culture surface for a particular cell line may allow the user to select a culture surface which includes a particular level of carboxylic acid functionality for that particular cell line. A method of analyzing the level of carboxylic acid functionality for a given cell line is described herein.

Any desired means for fabricating a surface chemical gradient on the substrate may be used. The preferred method for fabricating surface chemical gradients is by means of plasma deposition. Plasma deposition may be conducted by using a moving slot to separate plasma from the collecting substrate (and simultaneous control of two monomer gas ratios); this method has the advantage that it produces robust (stable) gradients and is scalable. In this fashion, a shielding apparatus having a slot or hole therein acts as a collimator of species from the plasma, i.e., by shielding a substantial portion of the surface of the collecting substrate. This method allows reactive species from the plasma to be deposited onto the surface of the collecting substrate only on a narrow area exposed by the slot or hole. It is not format (e.g. microchannels) or substrate dependent, and is compatible with existing semi-conductor fabrication technology; features that make for ready integration in biological experiments, and the basis for a high-throughput technology. Other methods of plasma deposition, including those previously described, may be incorporated as desired.

In one method, during plasma deposition, the deposition apparatus may be moved relative to the substrate and the supply of monomers may be changed, such that the relative concentration of monomer groups containing carboxylic acid in the polymer varies across the surface. The supply of monomers may be changed with different monomers being used and/or different intensities pf plasma being used (e.g., the plasma is pulsed). In this method, the surface may be plasma-deposited in such a fashion that there are discrete regions of plasma deposition on the surface, each region having a known concentration of carboxylic acid.

In a further method, such as that depicted in FIG. 5, the substrate 10 may have a plurality of plasma-polymerized treated regions 12, 14, 16. The substrate 10 may include may include two or more regions. Each region 12, 14, 16 may have a different concentration of carboxylic acid. The change in degree of concentration of carboxylic acid across the substrate 10, particularly, along the regions 12, 14, 16, defines the gradient 18. As described below, depending on observed cell activity in each of the regions 12, 14, 16, a concentration of carboxylic acid may be selected. More specifically, cells may be cultured on the regions 12, 14, 16 with there being observation of cell activity characteristics of interest (e.g., cell growth; cell attachment; and so forth). Depending on the observations, it may be determined that certain of the regions 12, 14, 16 produce more desirable results (i.e., more desirable levels of cell activity) than other of the regions 12, 14, 16. With this determination, plasma-polymerized secondary substrates 12A, 14A, 16A may be utilized, each corresponding to one of the regions 12, 14, 16 and each having a constant level of concentration of carboxylic acid. In this manner, experiments may be conducted on the secondary substrates 12A, 14A, 16A with a selected constant level of concentration of carboxylic acid being exposed to the cultured cells. Thus, by way of non-limiting example, the region 12 may a 2% concentration of carboxylic acid; the region 14 may a 5% concentration of carboxylic acid; and, the region 16 may a 7.5% concentration of carboxylic acid. In turn, the secondary substrate 12A is provided with a 2% concentration of carboxylic acid continuously thereacross; the secondary substrate 14A is provided with a 5% concentration of carboxylic acid continuously thereacross; and, the secondary substrate 16A is provided with a 7.5% concentration of carboxylic acid continuously thereacross. A kit may be provided including the substrate 10 and any one or more of the secondary substrates 12A, 14A, 16A.

The ability to maintain and cultivate pluripotent cells, including embryonic stem (ES) cells in a condition where they are capable of self-renewal plays a role in the development of cell therapy technologies. Various reports detail how the culture conditions for mouse ES (mES) and human ES (hES) may be manipulated to maintain these cells in an undifferentiated state. Significant differences between mES and hES have been commented upon, as well as common mechanisms in maintaining cell self renewal. It has been recently reported that the capacity of mES cells for self-renewal may be maintained by restricting the degree to which these cells spread. This result implies that self-renewal of mES cells can be maintained without the addition of additional factors to the culture media, such as leukaemia inhibitory factor (LIF) under conditions where the degree of cell spreading is limited.

Crude control over cell attachment and spreading may be exercised by modifying the adhesivity of the culture substrate by coating with different concentrations of serum proteins. Any level of serum coating may be incorporated as desired. For example, coating with 2.5% serum produces a weakly adhesive (WA) substrate, whereas coating with 0.1% gelatine and 10% serum produces a strongly adhesive (SA) substrate. Cell differentiation and cell spreading may be monitored. Cell differentiation may be monitored in any desired fashion, including by using a number of ES cell markers, such as Oct-4 and alkaline phosphatase (AP), both of which are lost on cell differentiation. Cell spreading may be monitored by any desired means, including by cortical F-actin staining Using these markers it may be shown that changes in cell shape precede, rather than result from, differentiation.

The limitation of this approach is the use of serum to control cell spreading. One requirement for the eventual use of stem cells in cell therapy and tissue engineering is the manipulation of cells under good manufacturing practice (GMP) and current Good Clinical Practice (GCP) without the use of xenobiotically-derived supplements to the basic culture media. In one particular embodiment, the culturing is achieved without the addition of animal (e.g. bovine) serum. Examples It would represent a very considerable advance if cells could be maintained in compact small colonies, retaining cell-cell contact through the influence of substratum chemistry alone (i.e. negating the need to condition the substratum surface with serum proteins). A study was conducted to demonstrate that cell attachment and the degree of cell spreading may be controlled by the surface density of carboxyl functionality. Further, the study was conducted to demonstrate that geometric control through control of surface carboxylic acid density may be used to control cell fate. Gradients of acid functionality were deposited by plasma deposition according to the method described above, where acid functionality was retained from monomer through to polymer by the use of low plasma input power.

A set of gradients were prepared using 1.3 cm coverslips. X-ray photoelectron spectroscopy was employed to determine how COOH concentration per 100 carbons varied across the coverslips. It was observed that the number of acid groups varied from 2.0% at (1.5 mm position) to 11.0% (12 mm position). E14 mES cells were cultured in serum free Advanced® media (Adv) on these surfaces for 7 days and were stained for AP. The coverslip was divided into five regions, with region 1 being the lowest % COOH (2%) and region 5 the highest % COOH (11%). The 5-region coverslip was then used to analyze the activity of cells for each of the regions. Cells were cultured on the coverslip for a period of 7 days, after which the various activities of the cells was observed and analyzed. Various activities of cells may be observed, including, for example, the degree of attachment, the level of growth, the level of AP activity, the level of cell spreading. The expression of particular proteins or markers (i.e., of differentiation or the like), and clustering of focal adhesions change of phenotype. Any other cellular activities that can feasibly be observed by the user may be used with the methods described herein. Once the user has evaluated and analyzed the various activities of the particular cell line in the various regions, the user may be able to determine the most suitable region for the particular cell line and activity desired. The region correlates to a particular level of carboxylic acid, which may allow the user to culture cells in that particular cell line more effectively. Separate secondary substrates may then be utilized with the particular cell line, with the secondary substrates having % COOH consistently thereacross corresponding to one of the regions.

The data show that at the end of the 7 day culture period, the degree of attachment and level of AP activity were dependent upon the position on the gradient, or moreover, the concentration of COOH. For instance, in regions 1 and 2 where COOH concentration is low, there was almost no cell attachment. In region 3, cells were able to attach but due to the low adhesivity of the substrate, the cells appeared to form compact, multilayered colonies. Under these conditions, AP staining is very intense, showing that most of the cells are undifferentiated. In region 5, adhesivity was strongest and under these conditions, the cells appeared to form flat, monolayered colonies with very weak AP staining, showing that many cells were differentiated. To investigate the colony morphology in more detail, the cells were imaged at higher magnification. Here it was seen that in region 3, there was little evidence of cell spreading on the substrate, whereas in region 4 the cells were slightly more spread. In region 5, cells displayed extensive spreading on the substrate. This experiment was repeated several times on identical gradients and apart from some 'edge effects', essentially the same results were obtained.

In order to determine the degree of cell spreading within each region of the gradient, the total number of cells within each of the colonies present within 2×1 cm$^2$ areas in each region were counted. The surface area of each colony was then divided by the number of cells in order to determine the average surface area of each cell within the colony. The results (Table 1) confirm that the degree of spreading may increase with increasing concentration of COOH. A and B show results from 2 different coverslips. This result shows that by varying the concentration of acid groups it may be possible to regulate the degree of cell spreading which in turn, affects mES cell differentiation.

The next objective was to investigate if other mouse ES cell lines behaved in a similar way when cultured on the COOH gradients and to investigate if cell attachment was affected by changing the culture medium. Although the Adv medium used previously is free of bovine serum, it does contain bovine albumin, which would make it unsuitable for the culture of therapeutic-grade human ES cells. For this reason, animal component free (ACF) media was used, which contained human recombinant albumin instead of bovine albumin.

The E14 and R1 mES cell lines were cultured in Adv and ACF media for 4 days on the COOH gradients. As expected, with E14 cells in Adv medium, cell attachment was seen at a comparable position on the coverslip as observed previously, and again, staining for AP reduces towards the bottom of the coverslip. In ACF medium, E14 ES cell attachment was reduced compared to that in Adv medium and colonies at the highest COOH end of the gradient remain AP positive. Interestingly, the behaviour of the R1 ES cells was markedly different from that of the E14 ES cells. It was found that cell attachment appeared stronger in ACF medium compared to Adv medium. This result was confirmed by culture on three separate coverslips for each cell line in both ACF and Adv medium. The results show that the degree of adhesion to the COOH substrate may be related to the cell line used and may vary with different culture media.

By controlling the surface adhesivity of the cell culture substratum, the degree of cell spreading may be able to be restricted, and may be used to maintain ES cells in a pluiripotent state. An experiment was conducted for two ES cell lines, where the differences were detected in the response to acid group surface density between the E14 and R1 mouse ES cell lines. The role of media was also highlighted, with E14 and R1 mES cells showing different responses to ACF and Adv. Extended culture for six or more passages on homogeneous surfaces showed that in ACF, R1 cells may prefer a lower surface acid % to E14 cells. Further, after extended culture on homogeneous surfaces, both E14 and R1 cells continued to express the undifferentiated ES cell markers, Oct-4, Nanog and AP[25]. This experiment showed that the COOH substrate may be able to support the long-term culture of these cells in serum free media. Thus, in a limited number of experiments, surface chemical gradients (fabricated by plasma on coverslips having varied levels of carboxylic acid) may be used to identify desired surface chemistries for the culture of different ES cell lines under a range of different media conditions. Moreover, the consistency of the results highlights the fact that the plasma fabrication method used to create the gradients may be highly reproducible. Surface chemical gradients produced by the plasma deposition techniques described herein aid the identification of synthetic substrates capable of supporting the self-renewal of human embryonic stem cells under GMP conditions.

TABLE 1

Cell area as a function of COOH concentration. The results A(1-5) and B(1-5) presented are from two different coverslips.

|    | Number of Cells | Number of Colonies | Average area ± SD ($\mu m^2$) |
|----|-----------------|--------------------|-------------------------------|
| A1 | 0               | 0                  |                               |
| A2 | 0               | 0                  |                               |
| A3 | 1186            | 6                  | 85.4 ± 33.5                   |
| A4 | 1708            | 19                 | 136 ± 35.7                    |
| A5 | 965             | 19                 | 255.2 ± 56.1                  |
| B1 | 0               | 0                  |                               |
| B2 | 0               | 0                  |                               |
| B3 | 2145            | 13                 | 93.9 ± 12.8                   |
| B4 | 1928            | 28                 | 142 ± 30.8                    |
| B5 | 749             | 23                 | 257 ± 96.9                    |

Fabrication of COOH Gradients Plasma-deposited gradients of octadiene (Sigma Aldrich) to acrylic acid (Sigma Aldrich) were fabricated onto 13 mm thermonox coverslips (Fisher Scientific). The shape of the gradient was controlled by the rate at which the octadiene:acrylic acid ratio was changed relative to the exposure of the coverslip. X-ray photoelectron spectroscopy (XPS) was under taken on a Kratos Ultra Instrument (Kratos, UK). Linescans were performed from the high octadiene (low acrylic acid) to high acrylic acid (low octadiene) end A 700×300 µm elliptical area was recorded every 1.5 mm across the sample giving 8 sampling points. The pass energy of the instrument was set to 160 eV for the C1s and O1s corelines. In the calculation of surface acid "density" it is assumed the plasma-deposit of acrylic acid is essentially poly (acrylic acid)-like and that the density of the plasma polymer is that of acrylic acid (1.05 g/cm3). The introduction of octadiene does not significantly change this density.

ES Cell Culture mES cell lines E14 and R1 were maintained on Nunc® tissue culture dishes coated with 10% (v/v) ES-tested fetal bovine serum (PAA laboratories) in either Adv medium, comprising Advanced® DMEM (Invitrogen) supplemented with 1000 U/ml LIF (Chemicon), 2 mM L-glutamine (Invitrogen) and 5 µM 2-mercaptoethanol (Invitrogen); or ACF medium comprising high glucose DMEM (Invitrogen) supplemented with 1000 U/ml LIF, 2 mM L-glutamine, 5 µM 2-mercaptoethanol, 100 mM monothioglycerol, 0.1% (w/v) PVA (polyvinyl alcohol) (Sigma), 1% (v/v) non-essential amino acids (Invitrogen), 1 ml/100 ml essential amino acids (Invitrogen), 1 ml/100 ml Insulin/Transferrin/Selenium (Invitrogen), 1 ml/100 ml Lipids (Invitrogen), 1 mM sodium pyruvate (Invitrogen) and 0.05 mg/ml human recombinant albumin (Sigma). Cells were sub-cultured every 3-4 days using enzyme-free dissociation buffer (Sigma) and medium was changed every 2 days. Cells were cultured in a humidified incubator at 37° C. and 10% CO2. Both E14 and R1 cells were used at passage 15-30. For gradient tests, ES cells were seeded at a density of 30,000 cells cm-2 and cultured for either 4 or 7 days on the gradients.

Alkaline Phosphatase Staining

ES cells were fixed in 4% (w/v) paraformaldehyde for 5 mins and washed ×3 in phosphate buffered saline (PBS). Following fixation, cells were equilibrated in 0.1M TrisHCl buffer pH 9.2 and incubated in 0.2 mg/ml Naphthol-AS-MX phosphate (Sigma) and 1 mg/ml Fast Red TR salt (Sigma) dissolved in the same buffer at room temperature for 15 min.

Microscopy

Low magnification digital images were acquired using a Nikon SMZ1000 stereoscopic dissecting microscope with a Nikon COOLPIX 990 camera. Higher magnification images were acquired using a Leica DM1L inverted microscope with 10×, 20× and 40× air objectives with a Canon Powershot 5 camera. Images for reproduction were prepared with Adobe Photoshop. For quantitative analysis of cell spreading, the total number of cells within each colony present within 2×1 cm2 areas from each of the 5 regions of the gradient were counted. The surface area of each colony was then divided by the number of cells in order to determine the average surface area of each cell within the colony.

REFERENCES

The following references, which are of background interest, are incorporated herein by reference:

[1] M. J. Chaudhury, G. M. Whitesides, Science, 1992, 256, 1539.
[2] J. Aizebnberg, A. J. Black, G. M. Whitesides, Nature, 1999, 398, 495.
[3] N. L. Jeon, S. K. W. Dertinger, D. T. Chiu, I. S. Choi, A. D. Stroock, G. M. Whitesides, Langmuir, 2000, 16, 8311.
[4] X. Y. Jiang, Q. B. Xu, S. K. W. Dertinger, A. D. Stroock, T. M. Fu, G. M. Whitesides, Anal. Chem., 2005, 77, 2338.
[5] S. Morgenthaler, S. Lee, S. Zürcher, N. Spencer, Langmuir, 2003, 19, 10459.
[6] B. Liedberg, M. Wirde, Y.-T. Tao, P. Tengvall, U. Gelius, Langmuir, 1997, 13, 5329.
[7] C. B. Herbert, T. L. McLernon, C. L. Hypolite, D. N. Adams, L. Pikus, C.-C. Huang, G. B. Fields, P. C. Letourneau, M. D. Distefano, W.-S. Hu, Chem. Biol., 1997, 4, 731.
[8] R. H. Terrill, K. M. Z. Y. Balss, P. W. Bohn, J. Am. Chem. Soc., 2000, 122, 988.
[9] S. H. Choi, B. Z. Newby, Langmuir, 2003, 19, 7427.
[10] X. Y. Jiang, Q. B. Xu, S. K. W. Dertinger, A. D. Stroock, T. M. Fu, G. M. Whitesides, Anal. Chem., 2005, 77, 2338.
[11] S. B. Kennedy, N. R. Wasburn, C. G. Simon Jr, E. J. Amis, Biomaterials, 2006, 27, 3817.
[12] B. Brandley, J. H. Sharper, R. L. Schnaar, Develop. Biol., 1990, 140, 161.
[13] M. S. Kim, K. S. Seo, G. Khang, H. B. Lee, Langmuir, 2005, 21, 4066.
[14] C. E. Kang, E. J. Gemeinhart, R. A. Gemeinhart, J. Biomed. Mater. Res., 2004, 71A, 403.
[15] J. D. Whittle, D. Barton, M. Alexander, R. D. Short, Chem. Comm., 2003, 14, 1766.
[16] A. G. Smith, J. K. Heath, D. D. Donaldson, G. G. Wong, J. Moreau, M. Stahl, D. Rogers, Nature, 1988, 336, 688.
[17] T. Burdon, A. Smith, P. Savatier, Trends Cell Biol., 2002, 12, 432.
[18] I. Ginis, Y. Luo, T. Miura, S. Thies, R. Brandenberger, S. Gerecht-Nir, M. Amit, A. Hoke, M. K. Carpenter, J. Itskovitz-Eldor, M. S. Rao, Develop. Biol., 2004, 269, 360.
[19] C. Anneren, C. A. Cowan, D. A. Melton, J. Biol. Chem., 2004, 279, 31590.
[20] N. Sato, L. Meijer, L. Skaltsounis, P. Greengard, A. H. Brivanlou, Nat. Med. 2004, 10, 55.
[21] A. J. Beck, L. O'Toole, R. D. Short, A. P. Ameen, F. R. Jones, J. Chem. Soc., Chem. Comm., 1995, 1053.
[22] K. L. Parry, A. G. Shard, R. D. Short, R. G. White, J. D. Whittle, A. Wright, Surface and Interface Analysis, 2006, 38, 1497.

What is claimed is:

1. A kit comprising:
   i) a plasma polymerized surface having first and second regions, said first region comprising a first concentration of carboxylic acid groups on said plasma polymerized surface and said second region comprising a second concentration of carboxylic acid groups on said plasma polymerized surface, wherein said first concentration and said second concentration are different;
   ii) a first plasma polymerized secondary substrate having carboxylic acid groups disposed consistently thereacross at a concentration equal to said first concentration; and,
   iii) a second plasma polymerized secondary substrate having carboxylic acid groups disposed consistently thereacross at a concentration equal to said second concentration.

2. The kit of claim 1, wherein said first region comprises a concentration of carboxylic acid groups from 2% to 11%.

3. The kit of claim 1, wherein said second region comprises a concentration of carboxylic acid groups from 2% to 11%.

4. The kit of claim 1, wherein said plasma polymerized surface having first and second regions comprises a known amount of polymer deposited on said surface.

5. The kit of claim 1, wherein said plasma polymerized surface comprises plasma deposited gradients of octadiene to acrylic acid.

6. The kit of claim 5, wherein said plasma polymerized surface comprises a known amount of octadiene and acrylic acid deposited in each of said first and second regions.

7. The kit of claim 6, wherein the amount of octadiene and acrylic acid deposited in each of said first and second regions is variable.

* * * * *